United States Patent
Yousef

(10) Patent No.: US 10,789,712 B2
(45) Date of Patent: Sep. 29, 2020

(54) METHOD AND SYSTEM FOR IMAGE ANALYSIS TO DETECT CANCER

(71) Applicant: MESC Health Ltd, Cardiff (GB)

(72) Inventor: Waleed Ahmed Yousef, Nasr (EG)

(73) Assignee: MESC Health Ltd, Cardiff Bay (GB)

( * ) Notice: Subject to any disclaimer, the term of this patent is extended or adjusted under 35 U.S.C. 154(b) by 185 days.

(21) Appl. No.: 16/031,426

(22) Filed: Jul. 10, 2018

(65) Prior Publication Data

US 2019/0019291 A1 Jan. 17, 2019

Related U.S. Application Data

(60) Provisional application No. 62/531,219, filed on Jul. 11, 2017.

(51) Int. Cl.
*A61B 6/00* (2006.01)
*A61B 8/08* (2006.01)
(Continued)

(52) U.S. Cl.
CPC ............ *G06T 7/0016* (2013.01); *A61B 6/502* (2013.01); *A61B 6/5217* (2013.01); *A61B 8/0825* (2013.01); *G06K 9/3241* (2013.01); *G06K 9/4642* (2013.01); *G06K 9/6223* (2013.01); *G06K 9/6226* (2013.01); *G06K 9/6247* (2013.01); *G06T 5/002* (2013.01); *G06T 5/009* (2013.01); *G06T 5/20* (2013.01); *G06T 5/40* (2013.01); *G06T 7/0014* (2013.01); *G06T 7/11* (2017.01); *G06K 2209/05* (2013.01); *G06T 2207/10116* (2013.01); *G06T 2207/20076* (2013.01); *G06T 2207/20081* (2013.01); *G06T 2207/30068* (2013.01)

(58) Field of Classification Search
None
See application file for complete search history.

(56) References Cited

U.S. PATENT DOCUMENTS 9,402,601 B1 * 8/2016 Berger ................ A61B 8/4472
2002/0141654 A1 * 10/2002 Rosales .................... G06T 5/20
382/261

(Continued)

OTHER PUBLICATIONS

El-Naqa, I. et al., "A Support Vector Machine Approach for Detection of Microcalcifications", IEEE Transactions on Medical Imaging, vol. 21, No. 12, Dec. 2002, pp. 1552-1563 (12 pages).

(Continued)

*Primary Examiner* — Soo Shin
(74) *Attorney, Agent, or Firm* — Ferguson Braswell Fraser Kubasta PC

(57) ABSTRACT

Detecting breast abnormalities includes receiving a first mammographic image having original pixels. A second mammographic image is generated by enhancing the first mammographic image. Enhancing the first mammographic image includes performing the following for each original pixel in at least a subset of the original pixels. A histogram is generated for a region surrounding the original pixel, the region defined by an enhancement sliding window. Using the histogram, a value of the original pixel is revised to obtain a revised value, and the revised value is stored in the second mammographic image. A breast abnormality location is detected based on the second mammographic image.

20 Claims, 13 Drawing Sheets

(51) Int. Cl.
*G06K 9/32* (2006.01)
*G06K 9/46* (2006.01)
*G06K 9/62* (2006.01)
*G06T 5/00* (2006.01)
*G06T 5/20* (2006.01)
*G06T 5/40* (2006.01)
*G06T 7/00* (2017.01)
*G06T 7/11* (2017.01)
*G16H 50/30* (2018.01)

(56) References Cited

U.S. PATENT DOCUMENTS

2008/0101678 A1* 5/2008 Suliga ............... G06K 9/4671 382/132
2009/0238426 A1* 9/2009 Fear .................. G06K 9/3216 382/128
2015/0193431 A1* 7/2015 Stoytchev ............ G16B 30/00 704/9
2018/0075628 A1* 3/2018 Teare ................... A61B 6/461
2018/0109698 A1* 4/2018 Ramsay ............. A61B 8/0825

OTHER PUBLICATIONS

Kamal, R. M. et al., Missed Breast Carcinoma: Why and How to Avoid?, Journal of the Egyptian National Cancer Institute, vol. 19, No. 3, Sep. 2007, pp. 178-194 (17 pages).

Kegelmeyer Jr., W.P. et al., "Computer-Aided Mammographic Screening for Spiculated Lesions", RSNA Radiology, vol. 191, No. 2, May 1994, pp. 331-337 (7 pages).

Muttarak, M. et al., Breast Carcinomas: Why are they missed?, Singapore Medical Journal, Oct. 2006, pp. 851-857, (7 pages).

Parkin, D. M. et al., "CA: A Cancer Journal for Clinicians, Global Cancer Statistics, 2002", Retrieved from the internet on Nov. 1, 2010, http://caonline.amcancersoc.org/cgi/content/full/55/2/74 pp. 74-108 (36 pages).

* cited by examiner

800 Original Image

820 Image Score Matrix on Original Image

METHOD AND SYSTEM FOR IMAGE ANALYSIS TO DETECT CANCER

CROSS-REFERENCE TO RELATED APPLICATIONS

This application claims priority, pursuant to 35 U.S.C. § 119(e), to U.S. Provisional Application No. 62/531,219, filed on Jul. 11, 2017, the entirety of which is incorporated by reference herein.

BACKGROUND

Detection of breast cancer, while the breast cancer is still small and confined to the breast, provides the best chance of effective treatment for women with the disease. Benefits of early detection include increased survival rate, increased treatment options and improved quality of life. To detect breast cancer, mammography is performed to capture an image of the breast tissue. In some cases, the breast cancer is not detected. Causes of missed breast cancer on mammography can be secondary to many factors including factors related to the patient (whether inherent or acquired), the nature of the malignant mass, poor mammographic techniques, or provider factors or interpretive skills of radiologists and oncologists (including perception and interpretation errors).

Perception error occurs when the lesion is included in the field of view and is evident but is not recognized by the radiologist. The lesion may or may not have subtle features of malignancy that cause the lesion to be less visible. Several factors may lead to misinterpretation, such as lack of experience, fatigue, or inattention. Misinterpretation may also occur if the radiologist fails to obtain all the views needed to assess the characteristics of a lesion or if the lesion is slow growing and prior images are not used for comparison.

SUMMARY

In general, in one aspect, one or more embodiments relate to a method for detecting breast abnormalities. The method includes receiving a first mammographic image having original pixels. A second mammographic image is generated by enhancing the first mammographic image. Enhancing the first mammographic image includes performing the following for each original pixel in at least a subset of the original pixels. A histogram is generated for a region surrounding the original pixel, the region defined by an enhancement sliding window. Using the histogram, a value of the original pixel is revised to obtain a revised value, and the revised value is stored in the second mammographic image. The method further includes detecting a breast abnormality location based on the second mammographic image.

In general, in one aspect, one or more embodiments relate to a system that includes a data repository for storing a first mammographic image and a computer processor connected to the data repository. The computer processor is for executing cancer detection software. The cancer detection software includes an image enhancer that is configured to obtain a first mammographic image having original pixels from the data repository and generate a second mammographic image by enhancing the first mammographic image. Enhancing the first mammographic image includes performing the following for each original pixel in at least a subset of the original pixels. A histogram is generated for a region surrounding the original pixel, the region defined by an enhancement sliding window. Using the histogram, a value of the original pixel is revised to obtain a revised value, and the revised value is stored in the second mammographic image. The cancer detection software is configured to detect a breast abnormality location based on the second mammographic image.

In general, in one aspect, one or more embodiments relate to a non-transitory computer readable medium that includes computer readable program code for detecting breast abnormalities. The computer readable program code is for receiving a first mammographic image having original pixels. A second mammographic image is generated by enhancing the first mammographic image. Enhancing the first mammographic image includes performing the following for each original pixel in at least a subset of the original pixels. A histogram is generated for a region surrounding the original pixel, the region defined by an enhancement sliding window. Using the histogram, a value of the original pixel is revised to obtain a revised value, and the revised value is stored in the second mammographic image. The computer readable program code is further for detecting a breast abnormality location based on the second mammographic image.

Other aspects of the invention will be apparent from the following description and the appended claims.

DETAILED DESCRIPTION

Figure 1:
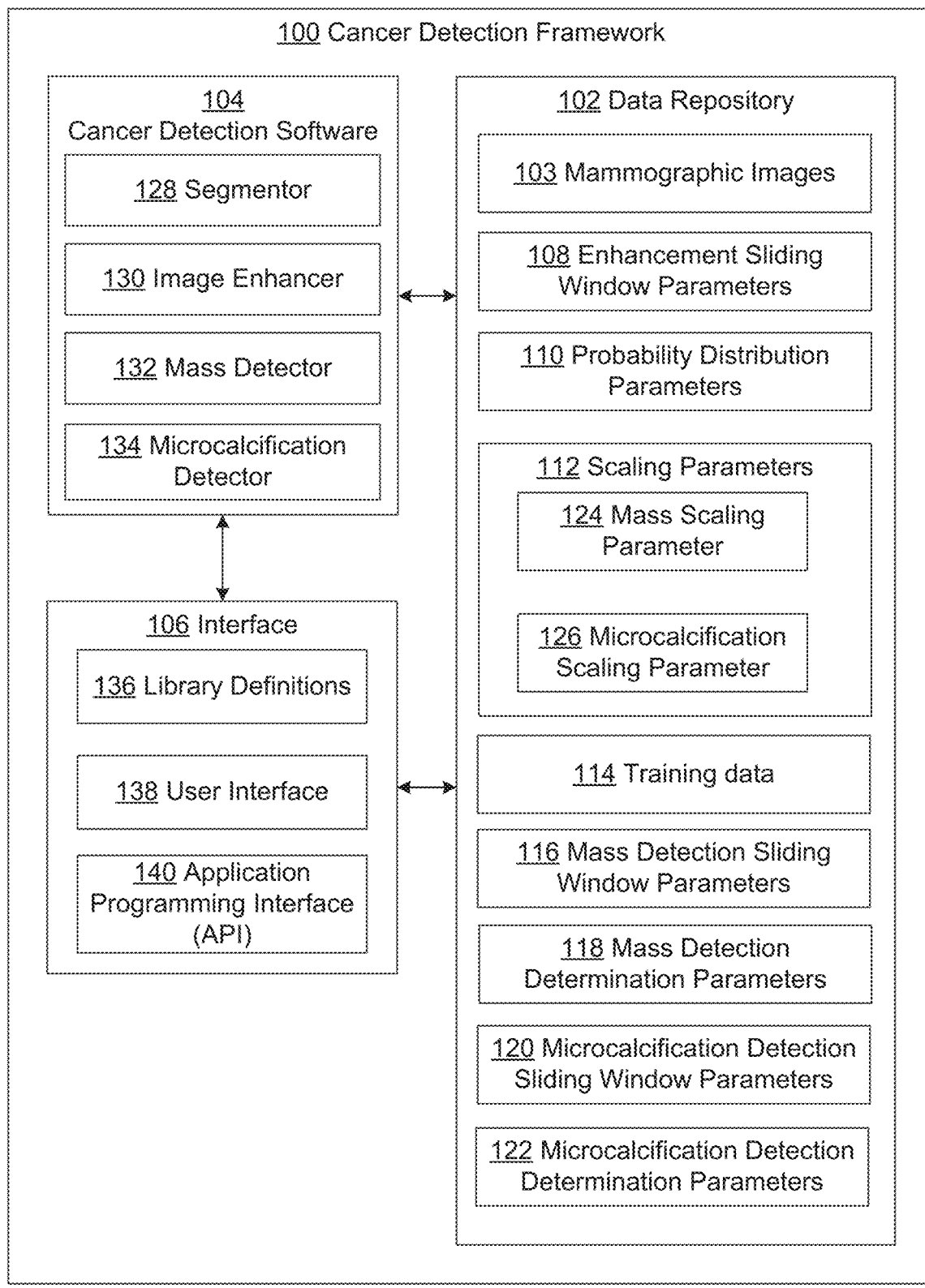
FIG. 1 shows a diagram of a system in one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the invention are directed to a computer aided detection for detecting breast abnormalities that may be indicative of cancer. Specifically, one or more embodiments are directed to a technique for a computing system to detect the location of the breast abnormality. By designing a computing system to process mammographic images, human errors that lead to missing breast carcinoma, such as poor perception or interpretation errors, are mitigated. One or more embodiments enhance a mammographic image by generating a localized histogram for each region surrounding an original pixel in the mammographic image. The value of the original pixel is revised using the histogram and is stored in a second mammographic image, which is then used to detect a breast abnormality location.

Turning to FIG. 1, FIG. 1 shows a diagram of a system in accordance with one or more embodiments of the invention. As shown in FIG. 1, the system includes cancer detection framework (100). The cancer detection framework (100) is a computing system that has hardware and software to detect locations of breast abnormalities. For example, the cancer detection framework (100) may be implemented using the computing system described below with reference to FIGS. 12A and 12B. As shown in FIG. 1, the cancer detection framework (100) includes a data repository (102), cancer detection software (104), and an interface (106). Each of these components is described below.

In one or more embodiments of the invention, the data repository (102) is any type of storage unit and/or device (e.g., memory, a file system, database, collection of tables, or any other storage mechanism) for storing data. Further, the data repository (102) may include multiple different storage units and/or devices. The multiple different storage units and/or devices may or may not be of the same type or located at the same physical site. In one or more embodiments, the data repository (102) includes mammographic images (103), enhancement sliding window parameters (108), probability distribution parameters (110), scaling parameters (112), training data (114), mass detection sliding window parameters (116), mass detection determination parameters (118), microcalcification detection sliding window parameters (120), and microcalcification detection determination parameters (122). One or more of the various parameters may be stored as part of the cancer detection software, such as in the instructions of the cancer detection software. By way of another example, one or more of the various parameters may be stored separately from the cancer detection software, such as in a configuration file.

The mammographic images (103) are images obtained using mammography. The techniques described herein may be applicable to any type of images, including two-dimensional (2D), three-dimensional (3D), sonar, x-ray, or any other images. Mammographic images (103) include a first mammographic image. A first mammographic image is an unenhanced image. In one or more embodiments, the first mammographic image is an unaltered image that is directly captured using mammography and stored. In one or more embodiments, the first mammographic image is the unaltered image after preprocessing is performed. The first mammographic image includes original pixels. The original pixels are pixels of the image that are unaltered or are preprocessed. The mammographic images (103) may include an enhanced mammographic image. The enhanced mammographic image may be referred to as a second mammographic image to distinguish the enhanced mammographic image from the first mammographic image. The enhanced mammographic image includes revised pixels having a revised value.

In one or more embodiments, mammographic images acquired from different mammography machines are of different clarity and quality for both human visual inspection and detection algorithms. Therefore, the image enhancement is performed to achieve uniform qualitative clarity to the radiologist and of the same quantitative standardization for the detection algorithms regardless to the producing mammography machine.

In one or more embodiments, the enhanced mammographic image is produced using a local histogram specification. The local histogram specification is defined by enhancement sliding window parameters (108). In particular, enhancement sliding window parameters (108) are parameters defining a size of a sliding window for generating the enhanced image. A sliding window is a definition of dimensions of a contiguous region surrounding a current pixel being processed. Stated another way, the pixels in the contiguous region change as dependent on the focus of the region, which may be the center pixel of the region. The size of the sliding window parameters is a portion of the total size of the first mammographic image and of a scaled image. For example, the sliding window as defined by the enhanced sliding window parameters (108) may have a height of 81 pixels and a width of 81 pixels. Sliding windows for generating the enhanced image that have other heights and widths may be used without departing from the scope of the technology. Further, the width may not equal the height for the size of the sliding window.

The enhanced mammographic image is generated using a local histogram specification, which is processed using an exponential distribution function and a corresponding cumulative distribution function. The probability distribution parameters (110) are parameters for the probability distribution function and the corresponding cumulative distribution function. For example, the probability distribution parameters (110) may include the number of bins for the histogram for the probability distribution function and the lambda, which is a parameter of the exponential distribution function.

The scaling parameters (112) define a scale size to scale the mammographic image. Different mammography machines produce mammographic images of varying sizes. The scaling parameters (112) define a uniform size for the mammographic image. For example, the scaling parameters (112) may include a standard height identifier that identifies a uniform height of the mammographic images. Additionally, or alternatively, the scaling parameters (112) may include a standard width identifier that identifies a uniform width of the mammographic images.

In one or more embodiments, the scaling parameters (112) include a mass scaling parameter (124) and a microcalcification scaling parameter (126). The mass scaling parameter (124) may be used to scale mammographic images to detect masses. The microcalcification scaling parameter (126) may be used to scale the mammographic image to detect microcalcifications.

Training data (114) includes mammographic images that are known to have mass sections and normal sections. A mass section of a mammographic image has a mass. A mass refers to any circumscribed lump in the breast, which may be benign or malignant (cancer). In some embodiments, the mass section of a mammographic image may have microcalcifications. In one or more embodiments, the normal section does not include any mass or microcalcification.

Specifically, the normal section is normal from the standpoint of cancer detection. In one or more embodiments, the mass section in the training data is related to a mass identifier indicating that the mass section includes a mass. In one or more embodiments, a normal section is related to a normal identifier indicating that the section is normal. The mass identifier and normal identifier may be assigned and/or verified by a human, such as a radiologist. In such embodiments, one or more embodiments may use supervised machine learning algorithms. In one or more embodiments, the mass section and normal section are in different mammographic images in the training data. Specifically, identified normal sections in the training data are not in the same mammographic images that have mass sections. In other embodiments, the same mammographic image may both a mass section and a normal section in the training image.

Continuing with the data repository (102) of FIG. 1, mass detection sliding window parameters (116) are sliding window parameters to define one or more sliding windows to detect masses. In some embodiments, multiple sliding windows may be used on the same mammographic image to detect masses as defined in the mass detection sliding window parameters. The mass detection sliding window parameters may further define how to combine information acquired using multiple sliding windows.

The mass detection determination parameters (118) are parameters that define how to detect a mass. In one or more embodiments, the mass detection is performed using machine learning. For example, the mass detection determination parameters may define how to score pixels in an image, whereby the score indicates a possible mass. In one or more embodiments, the mass detection is performed using a machine learning model. In such a scenario, the machine learning model defines how to assign scores to an image. The mass detection determination parameters (118) may define parameters of the machine learning model. For example, if k nearest neighbor is used, the mass detection determination parameters (118) may specify the value of k. The mass detection determination parameters (118) may further include a threshold for the score for thresholding whether the score indicates the presence of a mass.

The microcalcification detection sliding window parameters (120) are sliding window parameters to define one or more sliding windows to detect macrocalcifications. Microcalcification are detected based on regions in which the pixels whose very few close neighbors have high gray level, and the next surrounding neighbors have much lower level. Thus, the microcalcification sliding window parameters define at least two sliding windows. The first sliding window is a close sliding window. The second sliding window defines the surrounding neighbors. The second sliding window omits the region defined by the first sliding window. In other words, the second sliding window defined by the microcalcification sliding window parameters has a hole for the set of pixels in the first sliding window.

The microcalcification detection determination parameters (122) define a difference between a low level and a high-level indicative of microcalcification in the mammographic image.

Continuing with FIG. 1, the cancer detection software (104) is software that includes functionality to detect a presence of cancer from one or more mammographic images. The cancer detection software (104) includes a segmentor (128), an image enhancer (130), a mass detector (132), and a microcalcification detector (134). Each of these components is described below.

The segmentor (128) includes functionality to segment a mammographic image. Segmenting the mammographic image separates the pixels determined to be part of the breast from the pixels determined to be part of the background. For example, the segmentor may identify the pixels that are part of the background and remove the pixel or associate the pixel with a background identifier.

The image enhancer (130) includes functionality to enhance mammographic image. Specifically, the image enhancer (130) is configured to perform local histogram specification to create an enhanced image.

The mass detector (132) is configured to detect a mass in a mammographic image. In one or more embodiments, the mass detector is trained based on the training data.

The microcalcification detector (134) is configured to detect microcalcification in the mammographic image. In particular, the microcalcification detector (134) is configured to determine whether the contrast between different sets of neighboring pixels is indicative of microcalcification.

The cancer detection framework (100) further includes an interface (106) in accordance with one or more embodiments of the invention. The interface (106) corresponds to the various mechanisms by which applications and humans may interact with the cancer detection framework (100).

In one or more embodiments, the computer aided detection is machine independent, and can operate with any mammography machine. In particular, the cancer detection framework (100) may detect cancer in any digital mammography by normalizing and standardizing the mammographic image through the image enhancement techniques.

Further, the cancer detection framework (100) may be deployed as a dynamic linked library (DLL) for Windows systems, shared object (SO) library for Linux systems, and application programming interface for cloud services. Thus, a developer to use the cancer detection framework (100) by simply calling the functions existing in these forms of library (DLL, SO, or API).

In one or more embodiments, the cancer detection framework (100) is implemented as a library that may be imported into a third-party developer's application. In such embodiments, the components shown in FIG. 1 are library functions. In other words, a developer may create software that uses the library functions of the cancer detection framework (100) to detect breast abnormalities. As shown in FIG. 1, the interface (106) includes library definitions (136). The library definitions (136) identify how to access the library functions of the cancer detection framework (100), the inputs expected by the library functions and the outputs presented by the library functions. The user interface may be provided by the separate developer application that uses the cancer detection framework (100). As another example, the user interface may be provided by the cancer detection framework (100).

The cancer detection framework (100) is designed to be a library to be called by any programmer, using any programming language, whether developing an image viewer and GUI, doing a batch processing, or even using the library in scientific research and pure scientific computing. Therefore, the library functions produce an output suitable for any application, leaving the interfacing issues to the designer of the application of interest. For instance, many companies existing in the market design their commercial image viewers, yet without cancer detection framework (100) capabilities.

As described above, the cancer detection framework (100) may be deployed as a DLL or SO. When deployed as a DLL or SO, the cancer detection framework (100) is a local-host based library to be installed on any local computer, server, or network. The cancer detection framework (100) does not require internet connection when deployed as a DLL or SO and can operate on a local machine. Thus, developers may issue calls to the DLL or SO library definitions from within the developer's programming environment to add detection capabilities to the developer's applications.

The interface (106) may include an application programming interface (API) (140). The API (140) provides an interface for the cancer detection framework (100) to be accessible for cloud service. In one or more embodiments, the API (140) is established through a PHP scripting language layer. Thus, the API (140) makes the cancer detection framework (100) accessible by anyone with an internet connection. The API (140) may be an interface to a library, in which case the components of the cancer detection framework (100) are library functions. In such a scenario, the cancer detection framework (100) algorithms are compiled and deployed to the cloud server in either library forms (e.g., DLL or SO), then the API (140) acts as a cloud interface to either form of the library. For example, developers wishing to integrate the cancer detection framework (100) functionalities to the developer's software may call the functions of the cancer detection framework (100) from cloud through hypertext transport protocol (HTTP) requests rather than installing the actual library (the DLL or the SO) on the developer's local servers.

Although not shown in FIG. 1, the cancer detection framework may use OpenCL™ (Open Computing Language) to implement basic and core functionalities and execute on a graphics processing unit (GPU) for fast processing. OpenCL™ is a trademark of the Khronos Group, Inc. located in Beaverton Oreg. The OpenCL™ library may be called directly by the DLL or SO. Thus, computations for a single user and allows for concurrent multiple users may execute faster.

Further, also one or more embodiments may use wrappers, such as C # wrapper for DLL and C++ wrapper for SO in order to communicate with the PHP layer of the cloud-based API.

Continuing with the interface (106), the interface (106) includes a user interface (138). The user interface (138) provides a web interface for end-users, such as radiologists. The user interface (138) may be a graphical user interface. The graphical user interface may be configured to overlay, on the portion of the mammographic image in which cancer or microcalcification is detector, an indicator of the cancer. For example, the indicator of cancer may be a color coding. Further, the color coding may be based on the probability that cancer exists at the location. The user interface may present additional information, such as information identifying the mammographic image, and the parameters used to detect masses or microcalcifications in the mammographic image.

The interface (106) may implement a session-based storage approach. Specifically, users upload the user's mammographic images once, and the images are stored in the data repository (102). At the end of the session, the mammographic images are discarded. Further, the interface (106) includes security measures, such as using secure connections and secure socket layer certificates.

While FIG. 1 shows a configuration of components, other configurations may be used without departing from the scope of the invention. For example, various components may be combined to create a single component. As another example, the functionality performed by a single component may be performed by two or more components.

FIGS. 2-6 show flowcharts in accordance with one or more embodiments of the invention. While the various steps in these flowcharts are presented and described sequentially, one of ordinary skill will appreciate that some or all of the steps may be executed in different orders, may be combined or omitted, and some or all of the steps may be executed in parallel. Furthermore, the steps may be performed actively or passively. For example, some steps may be performed using polling or be interrupt driven in accordance with one or more embodiments of the invention. By way of an example, determination steps, e.g., Step 209 and Step 217 in FIG. 2, may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention.

Figure 2:
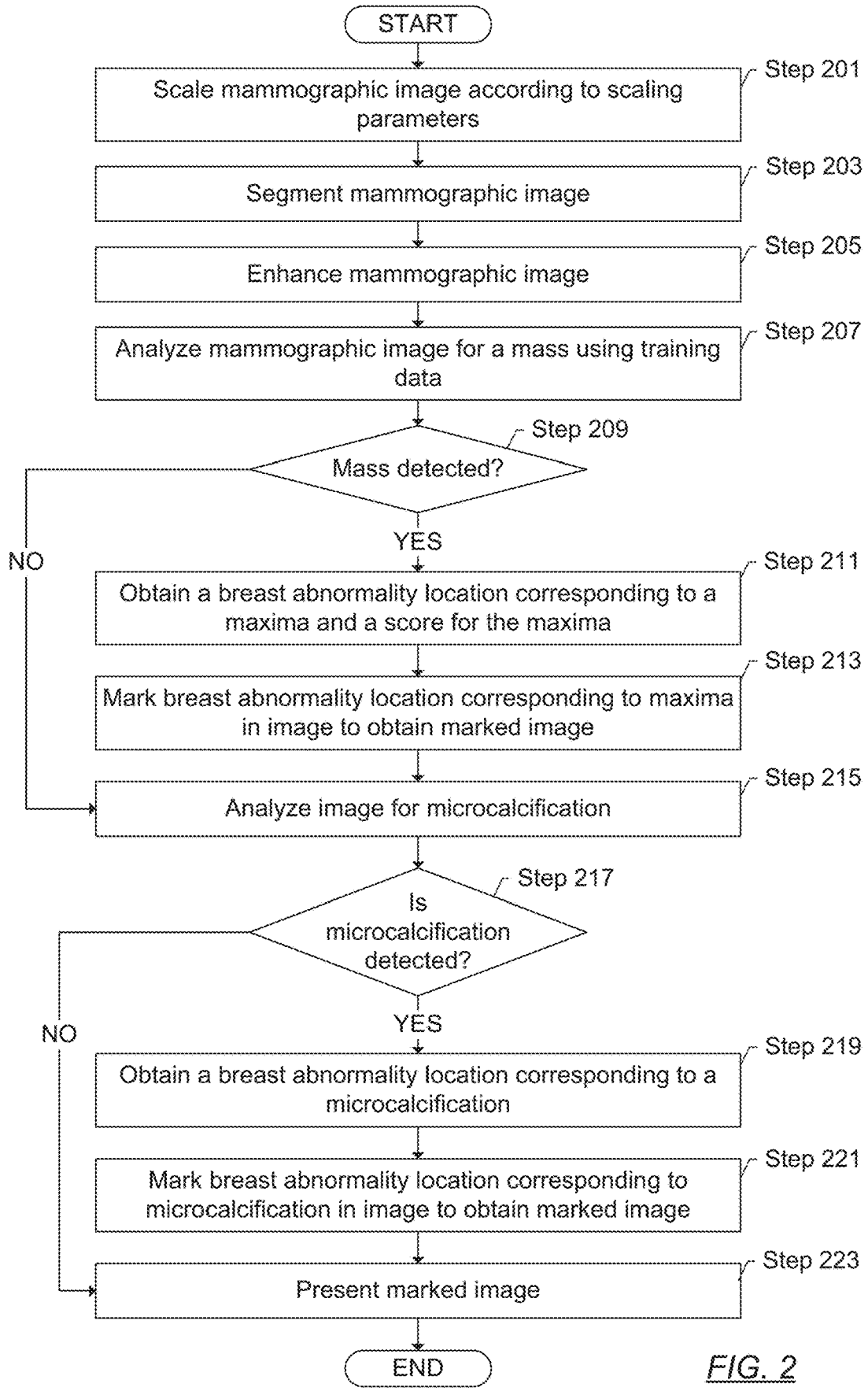
FIGS. 2, 3, 4, 5, and 6 show flowcharts in one or more embodiments.

FIG. 2 shows a flowchart for detecting a breast abnormality in accordance with one or more embodiments of the invention. In Step 201, the mammographic image is scaled according to scaling parameters. For example, if the scaling parameters specify a height of 230 pixels, the width may be set to maintain the aspect ratio. Different scaling algorithms may be used depending whether the size of the original image is greater or less than the specified size by the scaling parameters. Down sampling is performed when the size of the original image is greater than the specified size, and up scaling is performed when the size of the original image is less than the specified size. Filters may be applied to prevent artifacts, such as when down sampling is performed.

In Step 203, image segmentation is performed in one or more embodiments. Image segmentation may be performed by the segmentor. The image segmentation separates the portion of the image corresponding to the breast from the portion of the image corresponding to the background. For example, image segmentation may be performed based on the following properties of mammographic images. In a mammographic image, the breast is a contiguous region that is convex. The background is generally a single contiguous region but may be two contiguous regions. The pixels corresponding to the background may have the same or substantially the same color values, such as within the same color span. For example, the color values of the background may be within a predefined greyscale span that specify a minimum and/or maximum greyscale value. Thus, image segmentation may be performed by applying thresholding method to identify label pixels that are within the color span of the background. The image segmentation may then relabel background pixels that are within the convex space of pixels that are labeled as belonging to breast, such as by examining the neighbors of the pixel through one or more passes. Optimization techniques, such as by first identifying a proposed convex space, and labeling all pixels within the convex space as breast may be performed.

In Step 205, the mammographic image is enhanced in one or more embodiments. Image enhancement may be performed by the image enhancer. One or more embodiments use local histogram specification. In particular, for each original pixel in at least a subset of the pixels in the first mammographic image, a region is identified using an enhancement sliding window (i.e., a sliding window for image enhancement). The value of the pixel is modified based on the value of the pixels of the region to obtain a revised value. The revised value is stored. The subset of the pixels may correspond to the pixels in the mammographic image that are labeled as breast by the segmentor. The subset may correspond to a subsection of the portion labeled as breast.

In one or more embodiments, the histogram specification is performed to keep the pixel and the pixel's neighbors, within the region defined by the enhancement sliding window, to be of a predefined probability distribution with fixed parameters. Thus, the resulting mammographic image will have pixels within the same local histogram distribution with the same parameters. In one or more embodiments, an exponential distribution is used. The exponential distribution imposes more separation between the low gray level pixels and high-level pixels. Because cancer, whether a mass or microcalcification, is depicted in mammograms as the set of pixels with higher gray level than their neighbors, the exponential distribution helps in emphasizing the discrepancy. An example of a technique to perform image enhancement is described below with reference to FIG. 3.

Figure 4:
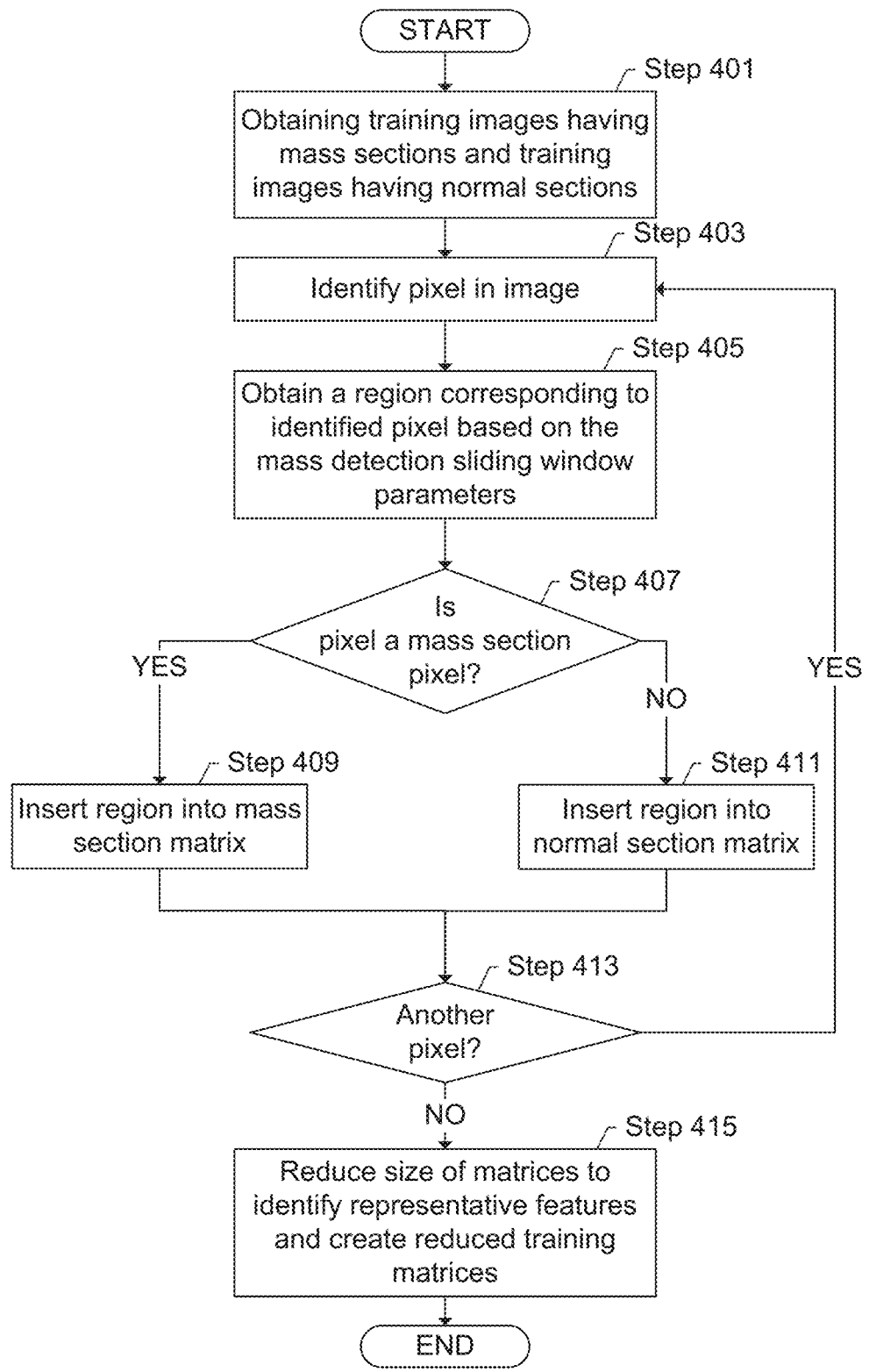
Figure 5:
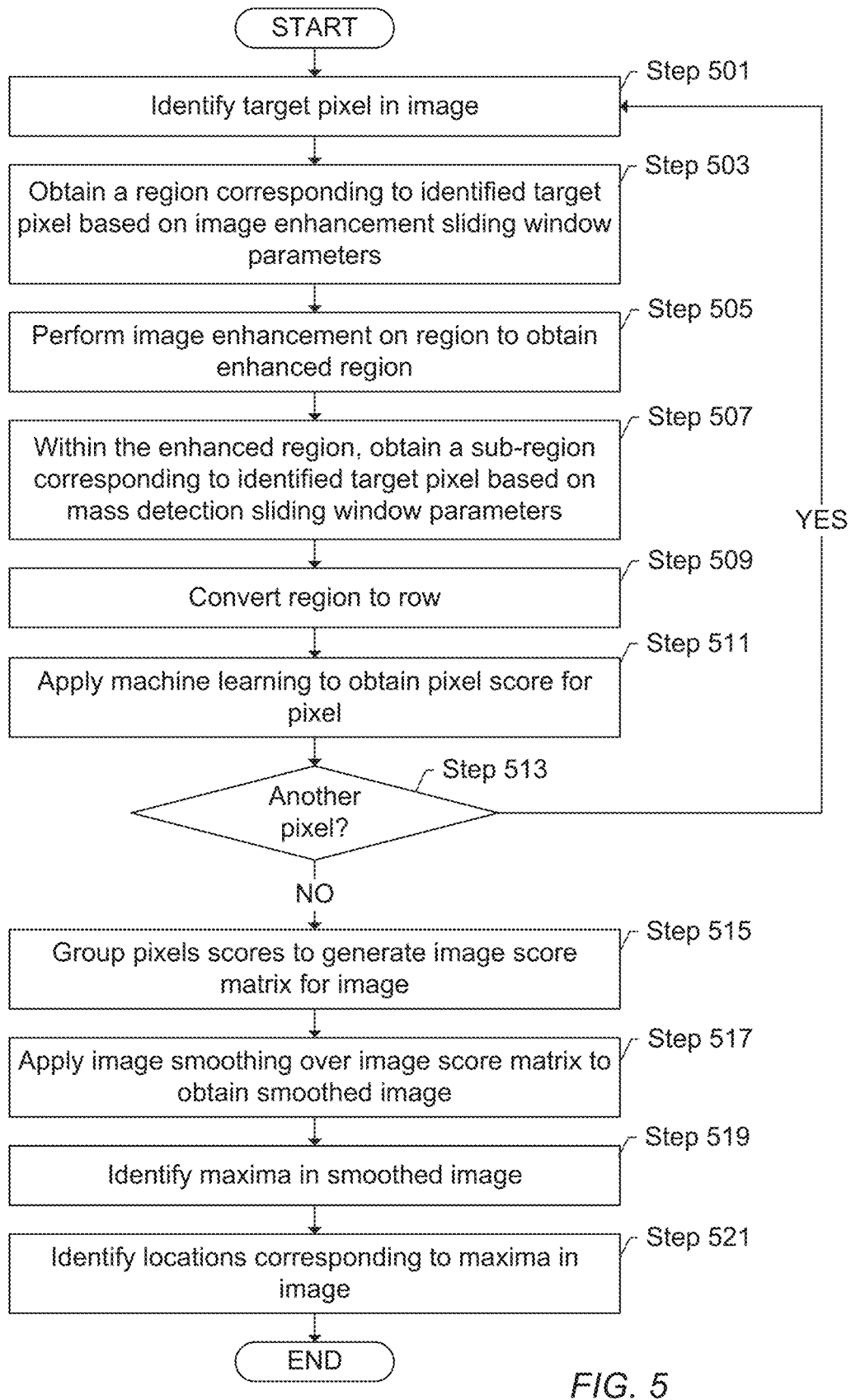

Continuing with FIG. 2, in Step 207, the mammographic image is analyzed for a mass using training data. A machine learning model is trained using training data having training images. In one or more embodiments, the training data includes thousands of images. Before the training phase, each image is annotated by a radiologist and the boundary of cancerous masses are marked and the ground truth was labeled. The algorithm works at the level of pixels without using any morphological features. Thus, the machine learning model uses a featureless (i.e., pixel-based) approach. The machine learning model is configured to score each pixel in the image based on the likelihood of the pixel corresponding to the location of the breast malignancy. FIG. 4 shows a flowchart for training the machine learning model in accordance with one or more embodiments of the invention. FIG. 5 shows a flowchart for detecting a mass in accordance with one or more embodiments of the invention.

Continuing with FIG. 2, in Step 209, a determination is made whether a mass is detected in accordance with one or more embodiments of the invention. First the score image is smoothed, then the maxima on the smoothed version is searched. For Step 209, the cancer detection framework may iterate through each pixel in the smoothed version of the image to identify the pixels having greater than the detection threshold. In other embodiments, the cancer detection framework may track the maxima score and the pixel with the maxima score while processing the smoothed image. The cancer detection framework may then determine whether the maxima score is greater than the detection threshold. If a mass is not detected, the flow proceeds to Step 215 to analyze the image for microcalcifications. If a mass is detected, the flow proceeds to Step 211 to obtain information about the mass.

In Step 211, the breast abnormality location corresponding to the maxima and the score for the maxima is obtained. The maxima are the pixel having the maxima score (i.e., the score that indicates the presence of a mass greater than the other assigned scores of the image). The maxima pixel belongs to the smoothed score image, not the score image itself. The breast abnormality location is the location of the pixel having the maxima. In one or more embodiments, the maxima may be set as any pixel in the image greater than the threshold. In such a scenario, each pixel having greater than the detection threshold is identified.

In Step 213, the breast abnormality location corresponding to the maxima in the image is marked to obtain a marked image. The marking applies an overlay on the enhanced image or the original image that makes the location of the mass conspicuous. As another example, the marking may be performed by creating a new mammographic image with the locations of the mass modified to a conspicuous color value, such as bright red or other obvious variation.

In Step 215, the image is analyzed for microcalcification. Clusters of microcalcifications are an early sign of possible cancer and are in general not palpable. Small clusters of amorphous or faint microcalcifications may be difficult to perceive. The cancer detection framework detects and marks microcalcification foci, even if the microcalcification foci that are not clustered. The output of the analyzing the image is whether microcalcification exists and the locations of each microcalcification foci.

Figure 6:
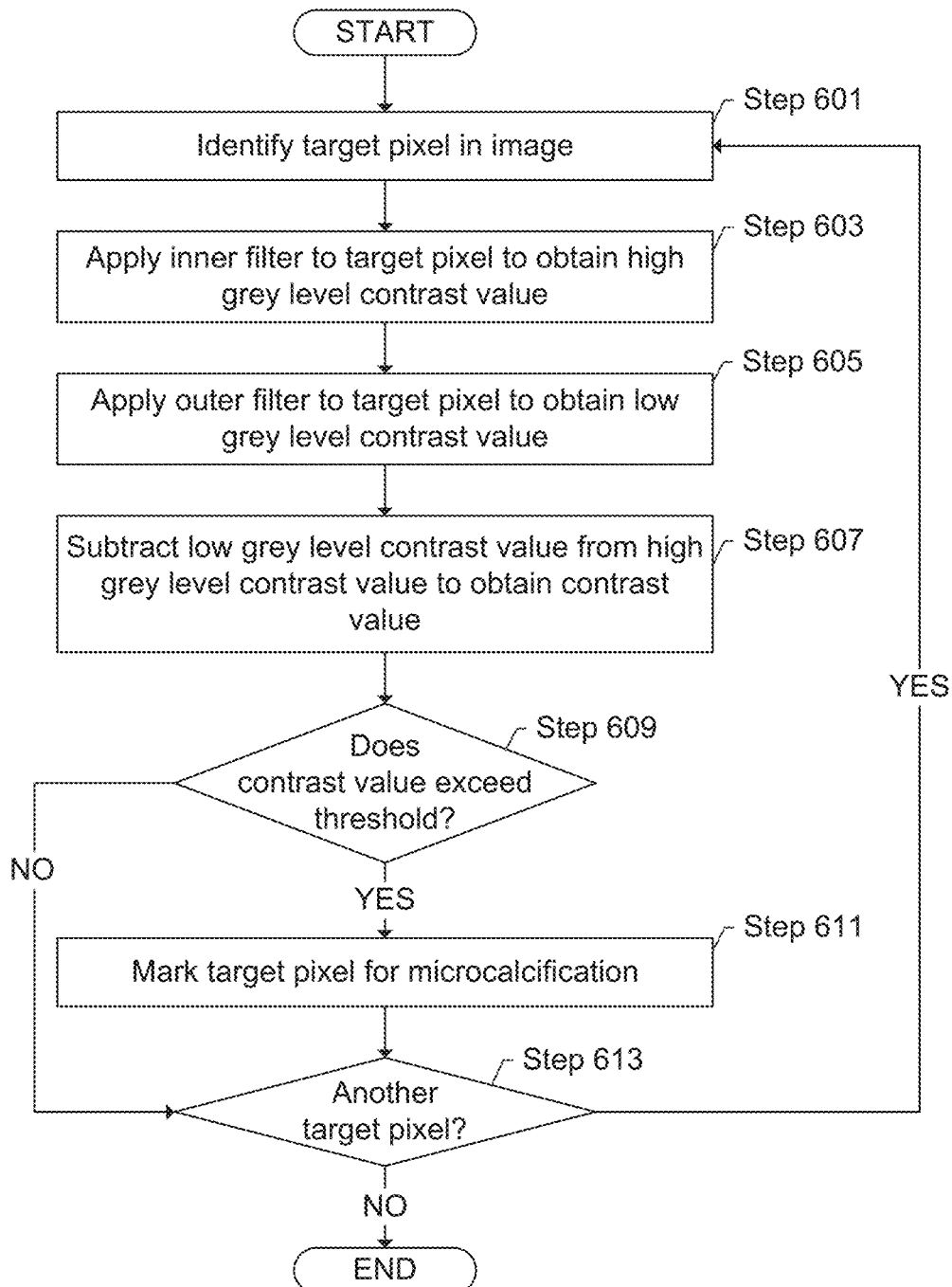

In one or more embodiments, a two-nested spatial filter is applied to detect the microcalcifications without using machine learning. Specifically, in one or more embodiments, microcalcification is detection based solely on image processing with no machine learning training and testing. The idea of the microcalcification detection in accordance with one or more embodiments is to detect the pixels whose very few close neighbors have high gray level, and the next surrounding neighbors have much lower level. FIG. 6 shows a flowchart for detecting microcalcifications in accordance with one or more embodiments.

In Step 217, a determination is made whether microcalcification is detected. If microcalcification is not detected, the flow proceeds to Step 223. If microcalcification is detected, the flow proceeds to Step 219.

In Step 219, the breast abnormality location corresponding to a microcalcification is obtained. In one or more embodiments, the result of Step 215 is the microcalcification foci. Thus, the obtained locations in Step 219 correspond to the microcalcifications.

In Step 221, the breast abnormality location corresponding to the microcalcification is marked in the image to obtain a marked image. Marking the breast abnormality location may be performed as discussed above with reference to Step 213.

In Step 223, the marked image is presented. For example, the marked image may be displayed to the user, transmitted to a developer application, sent via an internet, or otherwise presented. Thus, when using the cancer detection framework, the radiologist will see the score image besides, overlaying, or overlapping, the original image. The presentation enables inspecting the probability of having cancer in different breast regions. In addition, the center of cancerous masses may be marked in a conspicuous color on the original image. Radiologists can set a threshold level of aggressiveness for the score. For example, the centers of masses with scores greater than the detection threshold will be marked. Likewise, the radiologists may see the locations of the microcalcifications foci.

Figure 3:
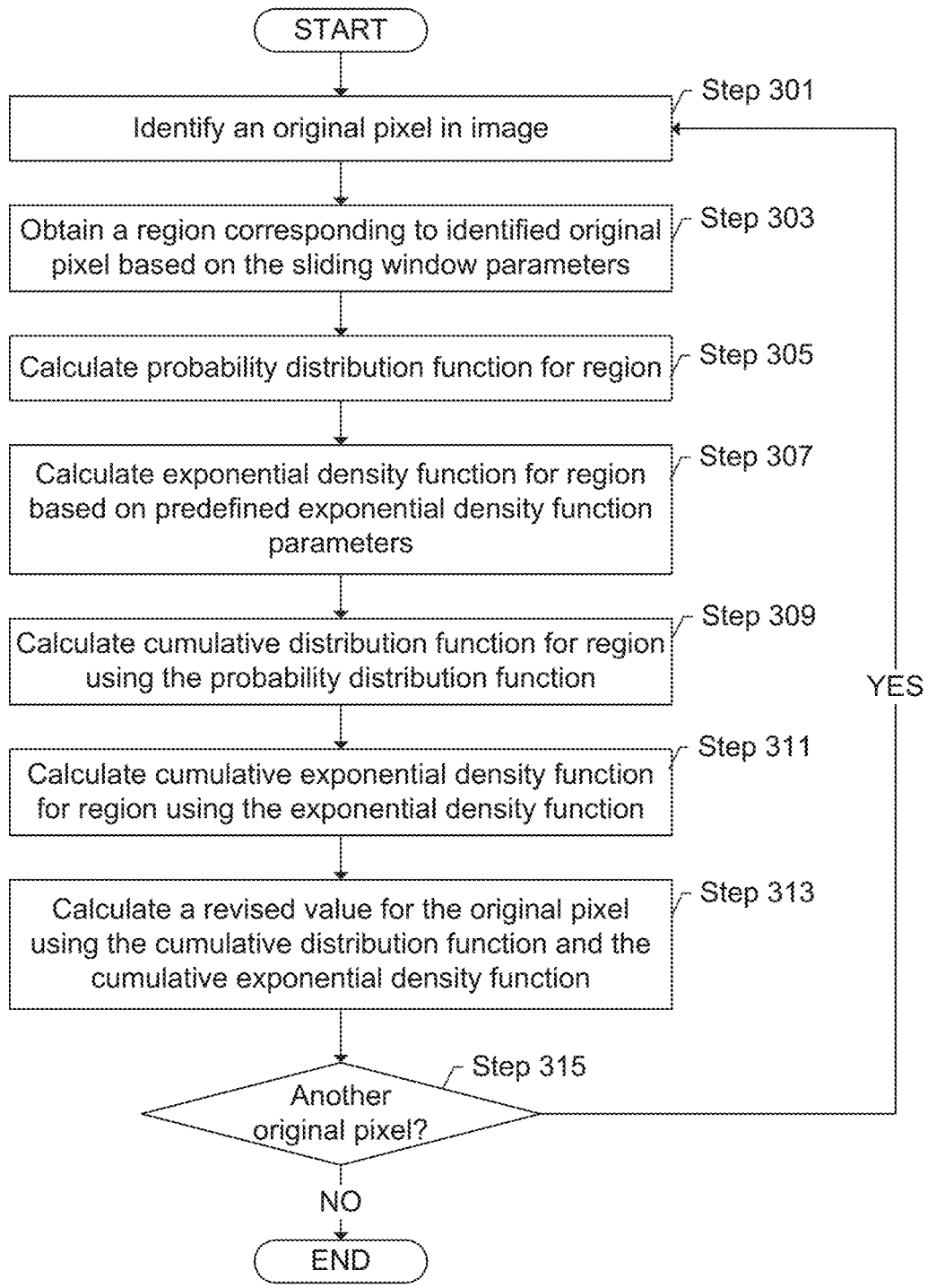

FIG. 3 shows a flowchart for enhancing an image in accordance with one or more embodiments. In Step 301, an original pixel of the image is identified. The process may iterate through the pixels labeled as breast. In Step 303, a region corresponding to the identified original pixel is obtained based on the sliding window parameters. The enhancement sliding window parameters specify the width and height of the region. For example, the enhancement sliding window parameters may specify a size of 81 centered around the identified original pixel. Thus, the region is of size $81^2$ or 6561 pixels.

In Step 305, a probability distribution function for the region is calculated in accordance with one or more embodiments of the invention. In one or more embodiments, a histogram is created for color value. For example, if 256 greyscale values exist for the first mammographic image, a histogram of 256 bins is created, where one bin exists for each greyscale value. For each pixel in the region, the value of the bin corresponding to the color value of the pixel is incremented by one. Thus, the resulting value of the bin is the number of pixels in the region having the color value of the bin.

In Step 307, an exponential density function is calculated for the region based on predefined exponential density function parameters. The exponential density function parameters may be the value of lambda. For example, lambda may be set as 10 for the exponential density function.

In Step 309, a cumulative distribution function is calculated using the probability distribution function. The value of the bin in the cumulative distribution function is the number of pixels having a color value less than or equal to the color value of the bin. The cumulative distribution function may be calculated by, for each bin, summing the values of the bins in the probability distribution function corresponding to a color value less than or equal to the current bin.

In Step 311, the cumulative exponential density function for the region is calculated using the exponential density function. The cumulative exponential density function may be calculated by, for each bin, summing the values of the bins in the exponential density function corresponding to a color value less than or equal to the current bin.

In Step 313, a revised value for the original pixel is calculated using the cumulative distribution function and the cumulative exponential density function. In one or more embodiments, the revised value is calculated using equation Eq. 1.

$$\text{Revised\_value} = \text{CDFexp}^{-1}(\text{CDFwin}(\text{current\_value})) \qquad \text{(Eq. 1)}$$

In equation Eq. 1, revised value is the revised color value of the original pixel. $\text{CDFexp}(t)$ is the cumulative exponential density function for color value t. $\text{CDFwin}(t)$ is the cumulative distribution function for color value t. Thus, the new gray level of the original pixel is inverse cumulative exponential density function of the cumulative distribution function of the color value of the pixel identified in Step 301. Specifically, for greyscale, the new gray level is the gray level at which the CDFexp will be equal to CDFwin of the previous gray level.

In Step 315, a determination may be made whether another pixel exists in accordance with one or more embodiments of the invention. As described above, the method may iterate through each pixel in the subset. If another pixel in the first mammographic image exists, the flow returns to Step 301 to process the next pixel.

FIG. 4 shows a flowchart for training a machine learning model for mass detection. In Step 401, training images having mass sections and training images having normal sections are obtained in accordance with one or more embodiments of the invention. The training images may be pre-marked by a radiologist.

In Step 403, a pixel of the image is identified. In one or more embodiments, for each image, the training of the machine learning model iterates through each pixel labeled as breast. In some embodiments, for images having mass sections, the machine learning model may iterate through only the pixels that are labeled by the radiologist as corresponding to the mass section.

In Step 405, a region corresponding to the pixel is obtained based on the mass detection sliding window parameters. Obtaining the region corresponding to a pixel may be performed in a same or similar manner to Step 303 of FIG. 3. In one or more embodiments, the mass detection sliding window parameters specify a sliding window that is smaller than the enhancement sliding window parameters. For example, if the enhancement sliding window parameters specify a width and height of 81 pixels for the sliding window, the mass detection sliding window parameters may specify a width and height of 21 pixels centered around the identified pixel. Thus, the total number of pixels in the sliding window is $21^2$ or 441.

In Step 407, a determination is made whether the pixel is a mass section pixel. In other words, a determination is made whether the radiologist marked the pixel as a mass section pixel. As mass section pixel may be any pixel in a mammographic image that has a mass and corresponds to breast. If the pixel is a mass section pixel, the flow proceeds to Step 409, where the region is inserted into the mass section matrix. If the pixel is not a mass section pixel, the flow proceeds to Step 411, where the region is inserted into the normal section matrix. The mass section matrix is a matrix for pixels corresponding to a mass section. The normal section matrix is a matrix for pixels corresponding to a normal section. Inserting a region into a respective matrix (e.g., mass section matrix, normal section matrix) may be performed as follows.

The region is flattened to a single row of features. A feature is the color level value of the corresponding pixel. To flatten the region, the first row of pixels in the region may be the first set of features, in order, in the single row, followed by the second row of pixels in the region, followed by the third row, etc. Thus, pixel at location (i, j) in region defined by identified pixel p may be at position of the matrix at location ($\text{row}_p$, i×j)). Thus, for a mass detection sliding window of size 441 pixels and a mammographic image having grey level values, a row represents the 441 gray levels of the surrounding window of the corresponding identified pixel.

In Step 413, a determination is made whether another pixel exists. The flow proceeds to process each pixel in the training images in one or more embodiments. If a determination is made that another unprocessed pixel exists, the flow returns to Step 403 to identify the next pixel to process in the training image.

If another pixel does not exist, the flow proceeds to Step 415. In Step 415, the size of the matrices is reduced using machine learning. In one or more embodiments, reducing the size of the matrices is performed using K-means clustering. The K-means clustering may be performed to reduce the number of rows of the matrices.

For example, a K-means clustering may be executed on each matrix to obtain the optimal Y representative rows for the mass section matrix and the normal section matrix. In other words, the size of each matrix will be reduced to Y×S, where S is the size of the region. In one or more embodiments, the value of Y is 100. For all mass section training images M, the mass section matrices of each training image are collected together to construct one larger matrix "MassCentroidList" of total size ((Y×M)×S). Similarly, for all normal section training images N, the normal section matrices of each training image are collected together to construct one larger matrix "NormalCentroidList" of total size ((Y× N)×S). As the number of rows is reduced, the number of columns may be reduced to select a subset of features. Columns may be reduced by taking the largest principal components. Specifically, Principal Component Analysis (PCA) is performed on the joined matrices [MassCentroidList; NormalCentroidList]. In one or more embodiments, the best number of features may be labeled R. For example, R may be 10 features (i.e., 10 selected columns). The R features (or vectors) are extracted (as PCVectors) and returned by the algorithm as (S×R) matrix. Thus, the mass section matrix and normal section matrix are then projected on PCVectors to be reduced in size to ((Y×M)×R) and ((Y×N)×R) respectively and returned by the algorithm as well.

FIG. 5 shows a flowchart for detecting a mass in a testing image. The testing image is the image having unknown mass or microcalcification. In Step 501, a target pixel in the image is identified. Identifying the target pixel may be performed as discussed above with reference to Step 301 of FIG. 3. In Step 503, a region corresponding to the identified target pixel is obtained based on the image enhancement sliding window parameters. In Step 505, image enhancement is performed on the region to obtain an enhanced region. Steps 503 and 505 may be performed as discussed above with reference to Step 205 and FIG. 3. In particular, for the testing image, Steps 503 and 505 of FIG. 5 may replace Step 205 of FIG. 2 in one or more embodiments.

In Step 507, within the target region, a sub-region corresponding to the identified target pixel is obtained based on the mass detection sliding window parameters. Step 507 may be performed in a same or similar manner to Step 405 of FIG. 4. As described above, the mass detection sliding window may be smaller than the enhancement sliding window.

In Step 509, the region is converted to a row. In other words, the region may be flattened to a single row of features. Flattening the region to a single row may be performed as discussed above with reference to FIG. 4. The single row of pixels is projected onto the .R principal components returned by the algorithm as PCVectors, as discussed in reference to FIG. 4. Thus, the number of columns is reduced in the single row of features to extract only R new features.

In Step 511, machine learning is applied to obtain a pixel score for the pixel. Each pixel is compared to the two extracted matrices from the training phase (MassCentroidList, NormalCentroidList) using a k nearest neighbor (KNN) algorithm. For example, the value of K may be 141. The KNN algorithm gives a score to each identified target pixel based on the MassCentroidList matrix and NormalCentroidList matrix. The score is normalized to a value between 0 and 1 to be used as a probability of being cancerous. The normalized score may be referred to as the pixel score.

In Step 513, a determination is made whether another unprocessed target pixel exists that is part of the breast. If another unprocessed target pixel exists, the flow returns to Step 501 to identify the next target pixel. If another unprocessed target pixel does not exist, the flow may proceed to Step 515.

In Step 515, the pixels scores are grouped to generate an image score matrix for the mammographic image. Specifically, the color value of each target pixel in the mammographic image is replaced or augmented with the pixel score for the target pixel. The augmentation may be performed on the first mammographic image or the enhanced mammographic image.

In Step 517, image smoothing may be applied over the image score matrix to obtain a smoothed image. Spatial filtering may be applied over the image score matrix to create the smoothed matrix. Thus, the image smoothing reduces outliers or data anomalies that may exist and are not representative of a mass. For example, a 10×10 smoothing filter that runs over the breast region of the image score matrix.

In Step 519, the maxima are identified in the smoothed image. After smoothing, the smoothed image is searched to find the maxima scores.

In Step 521, the locations corresponding to the maxima are identified and returned by the algorithm. The scores of the identified locations of the maxima are the probability of having cancer at the locations.

Although FIGS. 4 and 5 show a single mass detection sliding window size that is applied to the training images and the target or testing images, multiple mass detection sliding window sizes may be used. For example, the steps of FIG. 4 may be repeated for each mass detection sliding window size on the training images. Further, in the example, for each pixel, Steps 507-511 may be repeated for each sliding window size to obtain a pixel score for the sliding window sizes. The pixels scores for the various sliding window sizes may be mathematically combined to create a single pixel score for the target pixel. The mathematical combination may be an average, weighted average, etc. The flow may proceed as shown in FIG. 5 to create an image score matrix for the image. By way of an example, the sliding window sizes may be 9×9, 15×15, 21×21, 27×27, 33×33, 39×39, 45×45, 51×51, 57×57, and 63×63 pixels.

FIG. 6 shows a flowchart for microcalcification detection. In Step 601, a target pixel of the image is identified. Identifying a target pixel may be performed as discussed above with reference to Step 501 of FIG. 5. In Step 603, the inner filter is applied to obtain a high grey level contrast value. In one or more embodiments, the maximum color value in the inner filter region is the high grey level contrast value.

In Step 605, an outer filter is applied to the target pixel to obtain a low grey level contrast value. In one or more embodiments, the minimum color value in the outer filter region is the low grey level contrast value. Further, in one or more embodiments, the height and width of the outer filter may be three times the height and width of the inner filter.

In Step 607, the low grey level contrast value is subtracted from the high grey level contrast value to obtain a contrast value. In Step 609, a determination is made whether the contrast value exceeds a threshold. In particular, a determination is made whether the contrast value is greater than a threshold of allowed contrast. If the contrast value is greater than the threshold, then the pixel is marked for microcalcification in Step 611.

In Step 613, a determination is made whether another target pixel exists. In particular, the flow proceeds to process each pixel in the breast region. Based on the detected locations of microcalcifications, sub-regions of the breast may be identified that have microcalcifications. The foci of the sub-regions may be identified based on being in the center of the sub-region or having the largest contrast value for the sub-region.

FIGS. 7A-7B, 8A-8C, 9 and 10 show examples in accordance with one or more embodiments of the invention. The following are examples for explanatory purposes only and not intended to limit the scope of the invention.

Figure 7A:
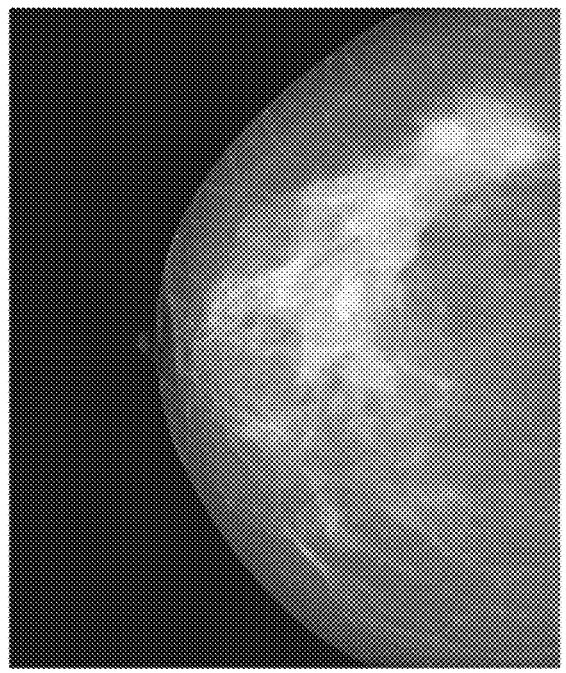
FIGS. 7A and 7B show an example in one or more embodiments.
Figure 7B:
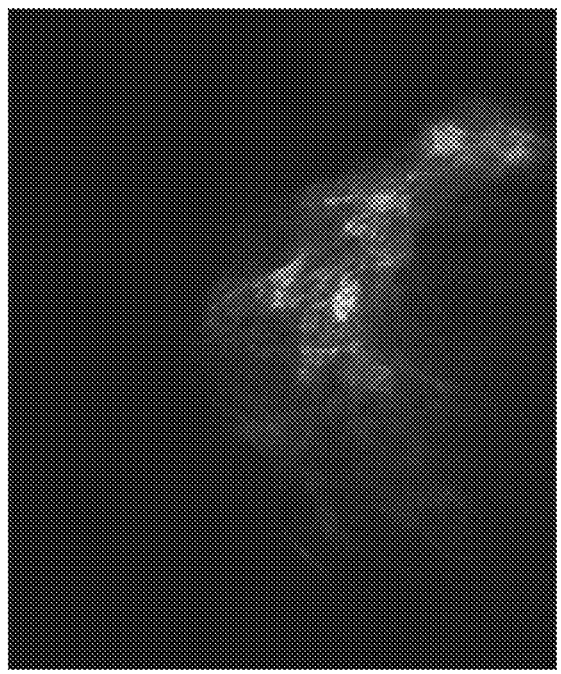

FIGS. 7A and 7B show an example of image enhancement. In particular, FIG. 7A shows an original image (700). FIG. 7B shows the result of applying image enhancement to the original image of FIG. 7A to create an enhanced image (750). The technique to create is the enhanced image in FIG. 7B is described above with reference to FIG. 3.

Figure 8A:
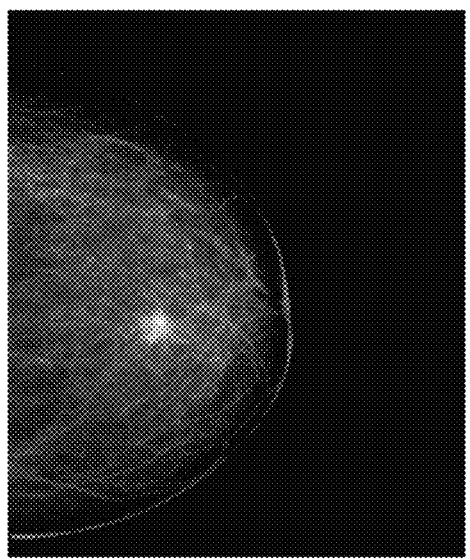
FIGS. 8A, 8B, and 8C show an example in accordance with one or more embodiments.
Figure 8B:
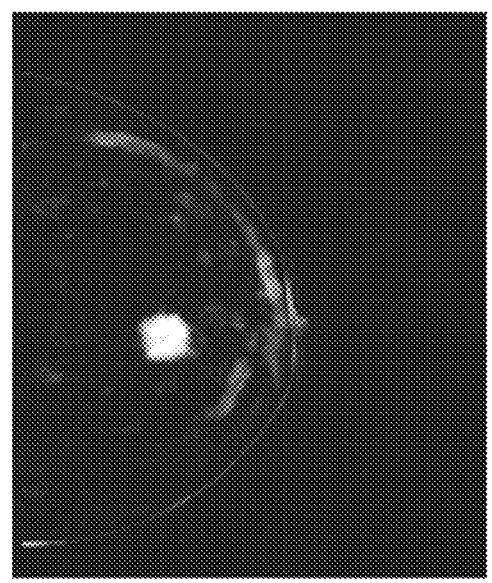
Figure 8C:
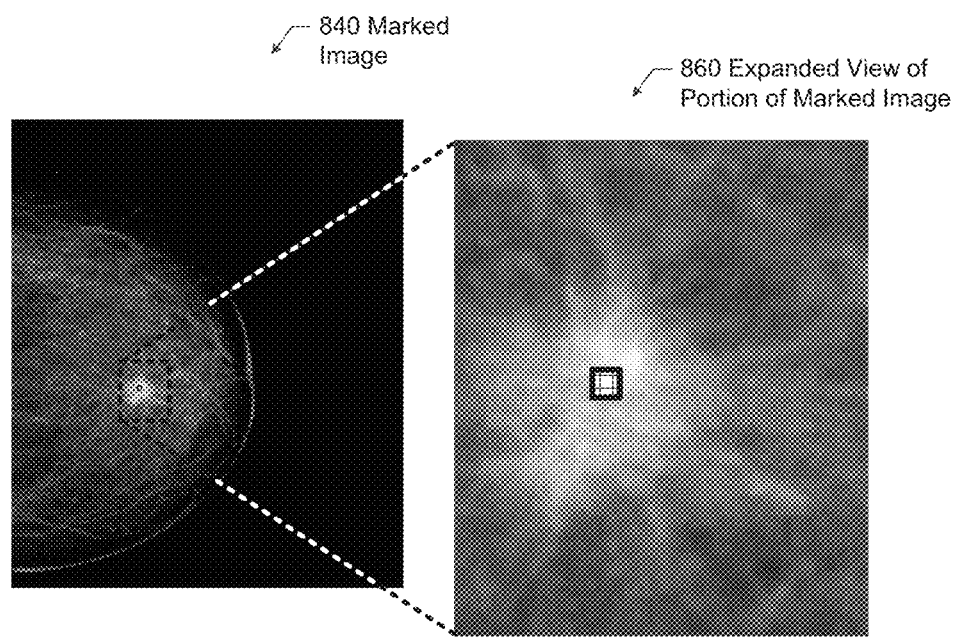

FIGS. 8A, 8B, and 8C show an example of mass detection in one or more embodiments of the invention. FIG. 8A shows the original image (800). FIG. 8B shows the image score matrix (820) overlaid on the original image. In other words, the pixels are encoded based on the pixel score. As shown in FIG. 8B, pixels having a low score have a low score greyscale value. A section of FIG. 8B is white denoting a high pixel score.

FIG. 8C shows a marked image (840) generated from the image score matrix. FIG. 8C also shows an expanded view (860) of the image score matrix with the maxima location marked. For the purposes of the example only, the marking uses a pattern surrounded by a thick line. When in use, the marking may be a high contrasting color value that conspicuously identifies the location.

Figure 9:
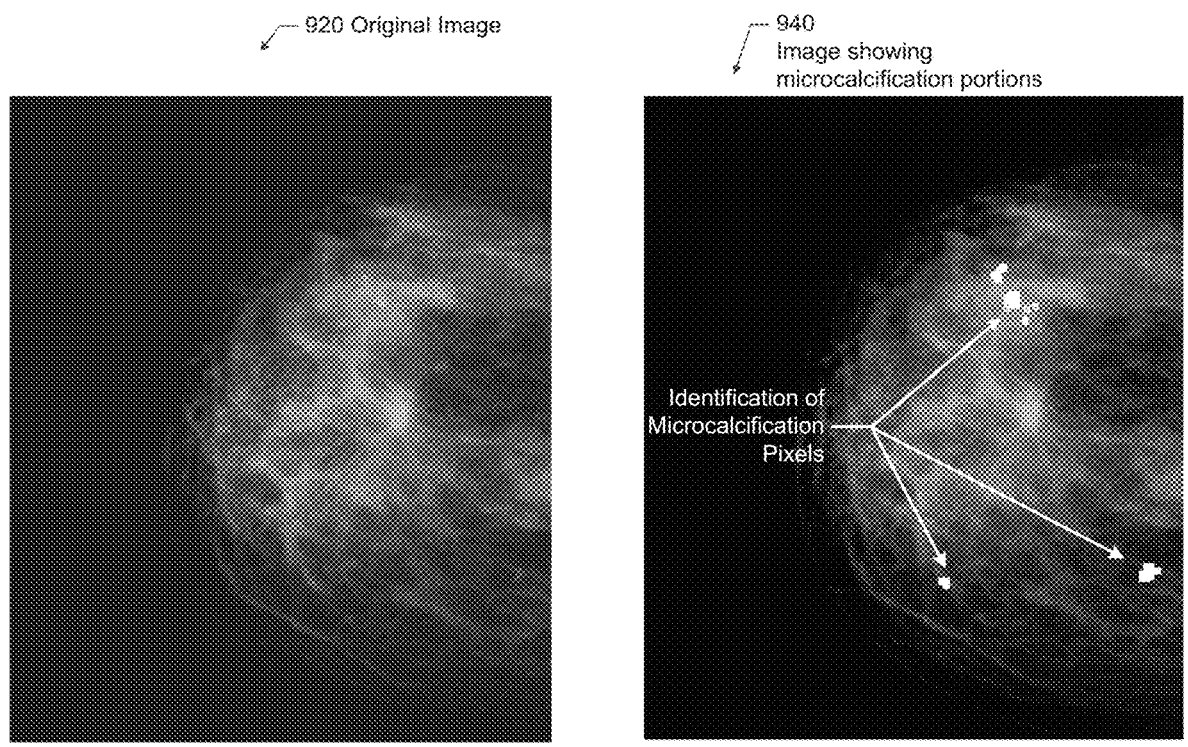
FIGS. 9 and 10 show examples in accordance with one or more embodiments of the invention.

FIG. 9 shows an example of microcalcification detection. In particular, FIG. 9 shows an original image (920) and an image showing microcalcification portions (940) identified using the steps of FIG. 6.

Figure 10:
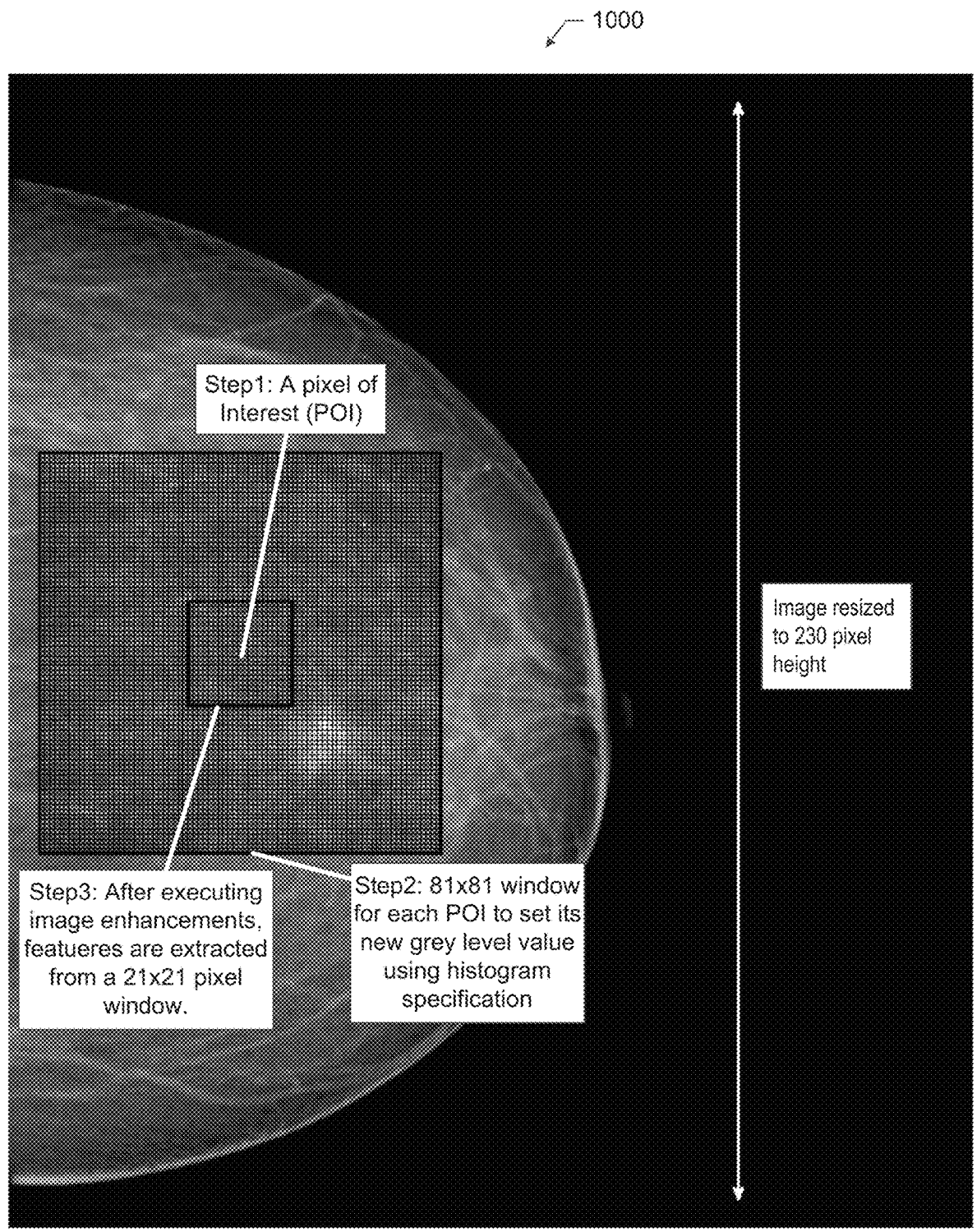

FIG. 10 shows an example (1000) of the image enhancement and mass detection. An image is reduced in size to 230-pixel height. Then the breast is segmented from the background. For each pixel (POI) in the breast region, a surrounding window of size 81×81 is used for local histogram specification to find the new gray level of the POI. Mass detection is pursued after histogram specification using another sliding window of size 21×21 centered around each POI, where its features will be a vector of the whole 21×21 grey levels.

Figure 11:
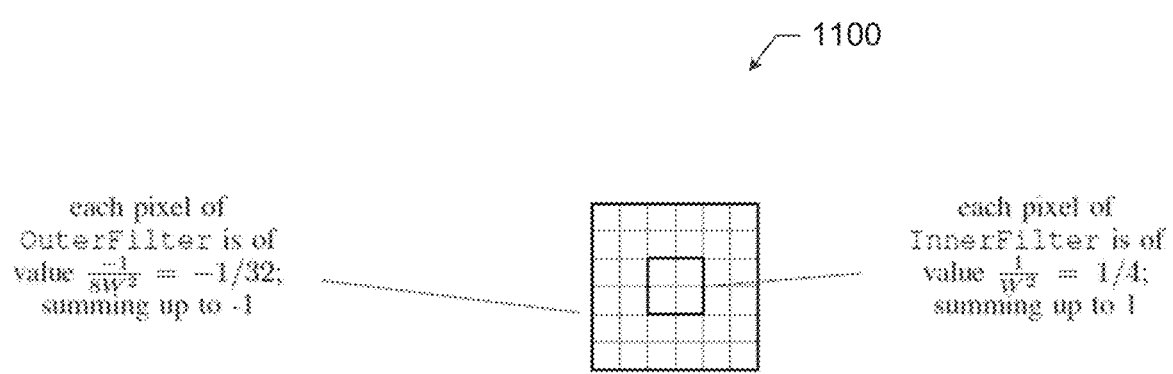
FIG. 11 shows an example in accordance with one or more embodiments of the invention.

FIG. 11 shows an example (1100) of the inner and outer filters for microcalcification detection. Filter of microcalcification detection is composed of two filters. An inner filter is of size W×W and outer of size 3W×3W, where W is chosen to be 2 pixels in the example of FIG. 11.

Figure 12A:
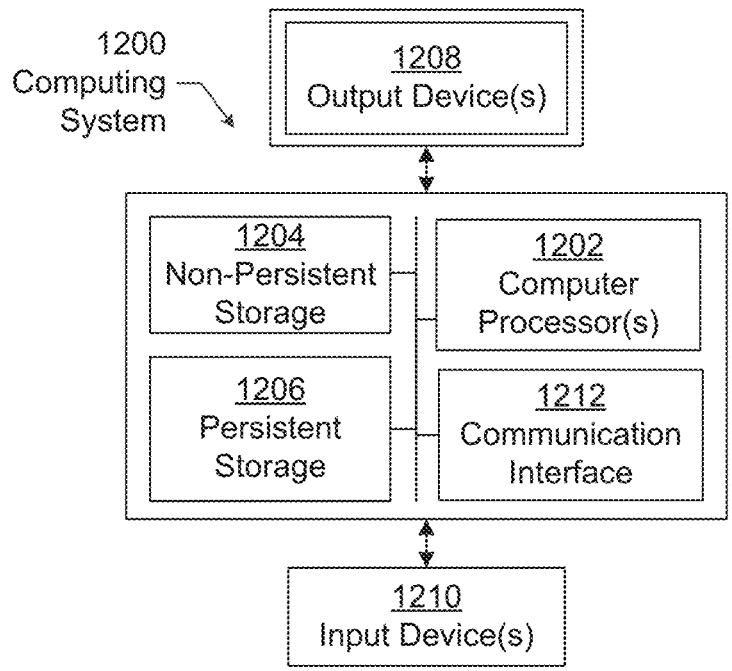
FIGS. 12A and 12B show a computing system in accordance with one or more embodiments of the invention.

Embodiments of the invention may be implemented on a computing system. Any combination of mobile, desktop, server, router, switch, embedded device, or other types of hardware may be used. For example, as shown in FIG. 12A, the computing system (1200) may include one or more computer processors (1202), non-persistent storage (1204) (e.g., volatile memory, such as random access memory (RAM), cache memory), persistent storage (1206) (e.g., a hard disk, an optical drive such as a compact disk (CD) drive or digital versatile disk (DVD) drive, a flash memory, etc.), a communication interface (1212) (e.g., Bluetooth interface, infrared interface, network interface, optical interface, etc.), and numerous other elements and functionalities.

The computer processor(s) (1202) may be an integrated circuit for processing instructions. For example, the computer processor(s) may be one or more cores or micro-cores of a processor. The computing system (1200) may also include one or more input devices (1210), such as a touchscreen, keyboard, mouse, microphone, touchpad, electronic pen, or any other type of input device.

The communication interface (1212) may include an integrated circuit for connecting the computing system (1200) to a network (not shown) (e.g., a local area network (LAN), a wide area network (WAN) such as the Internet, mobile network, or any other type of network) and/or to another device, such as another computing device.

Further, the computing system (1200) may include one or more output devices (1208), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (1202), non-persistent storage (1204), and persistent storage (1206). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

Figure 12B:
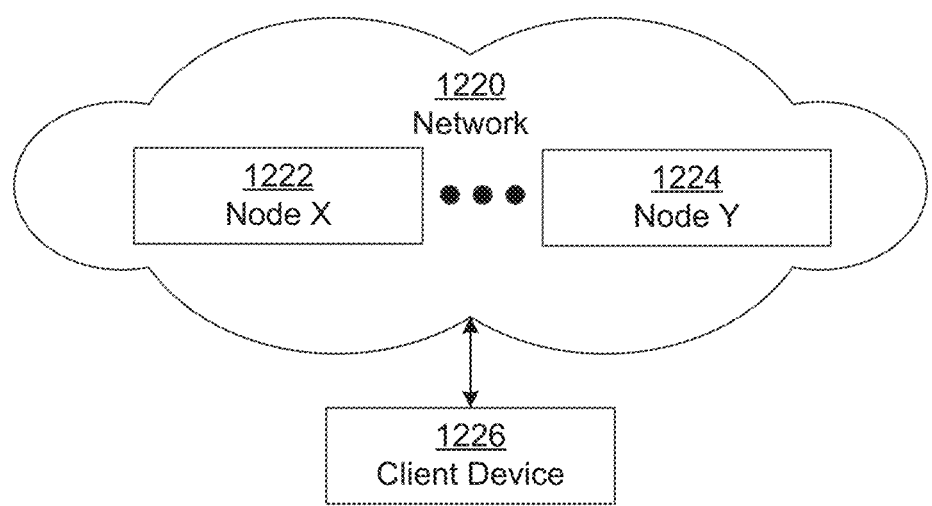

The computing system (1200) in FIG. 12A may be connected to or be a part of a network. For example, as shown in FIG. 12B, the network (1220) may include multiple nodes (e.g., node X (1222), node Y (1224)). Each node may correspond to a computing system, such as the computing system shown in FIG. 12A, or a group of nodes combined may correspond to the computing system shown in FIG. 12A. By way of an example, embodiments of the invention may be implemented on a node of a distributed system that is connected to other nodes. By way of another example, embodiments of the invention may be implemented on a distributed computing system having multiple nodes, where each portion of the invention may be located on a different node within the distributed computing system. Further, one or more elements of the aforementioned computing system (1200) may be located at a remote location and connected to the other elements over a network.

Although not shown in FIG. 12B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (1222), node Y (1224)) in the network (1220) may be configured to provide services for a client device (1226). For example, the nodes may be part of a cloud computing system. The nodes may include functionality to receive requests from the client device (1226) and transmit responses to the client device (1226). The client device (1226) may be a computing system, such as the computing system shown in FIG. 12A. Further, the client device (1226) may include and/or perform all or a portion of one or more embodiments of the invention.

The computing system or group of computing systems described in FIGS. 12A and 12B may include functionality to perform a variety of operations disclosed herein. For example, the computing system(s) may perform communication between processes on the same or different system. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, only one authorized process may mount the shareable segment, other than the initializing process, at any given time.

Other techniques may be used to share data, such as the various data described in the present application, between processes without departing from the scope of the invention. The processes may be part of the same or different application and may execute on the same or different computing system.

Rather than or in addition to sharing data between processes, the computing system performing one or more embodiments of the invention may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the invention, may extract one or more data items from the obtained data. For example, the extraction may be performed as follows by the computing system in FIG. 12A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail-such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 12A, while performing one or more embodiments of the invention, may perform data comparison. Data comparison may be used to compare two or more data values (e.g., A, B). For example, one or more embodiments may determine whether $A>B$, $A=B$, $A!=B$, $A<B$, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments of the invention, A and B may be vectors, and comparing A with B requires comparing the first element of vector A with the first element of vector B, the second element of vector A with the second element of vector B, etc. In one or more embodiments, if A and B are strings, the binary values of the strings may be compared.

The computing system in FIG. 12A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 12A may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions presents only a few examples of functions performed by the computing system of FIG. 12A and the nodes and/or client device in FIG. 12B. Other functions may be performed using one or more embodiments of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for detecting breast abnormalities, comprising:
    receiving a first mammographic image comprising a plurality of original pixels;
    generating a second mammographic image by enhancing the first mammographic image, wherein enhancing the first mammographic image comprises:
        for each original pixel in at least a subset of the plurality of original pixels:
            generating a histogram for a first region surrounding the original pixel, the first region defined by an enhancement sliding window, and revising, using the histogram, a value of the original pixel to obtain a revised value, the generating the histogram and revising the value comprising:
                calculating, for the first region, a probability density function;
                calculating, for the first region, an exponential density function;
                calculating, for the first region, a cumulative distribution function using the probability density function;
                calculating, for the first region, a cumulative exponential density function using the exponential density function; and
                calculating the revised value for the first region using the cumulative distribution function and the cumulative exponential density function, and
            storing the revised value in the second mammographic image; and
    detecting a breast abnormality location based on the second mammographic image.

2. The method of claim 1, further comprising: scoring a plurality of target pixels in the second mammographic image.

3. The method of claim 1, further comprising:
    obtaining a plurality of training images comprising a first subset of mass section pixels and a second subset of normal section pixels, the first subset of mass section pixels corresponding to a cancerous mass in the plurality of training images, the second subset of normal section pixels corresponding to a normal section in the plurality of training images;

for each mass section pixel in the first subset:
identifying a second region corresponding the mass section pixel, and
insert, into a mass section matrix, a row of pixel values that are in the second region; and for each normal section pixel in the second subset:
identifying a third region corresponding the normal section pixel, and
insert, into a normal section matrix, a row of pixel values that are in the third region, and detecting, using the normal section matrix and the mass section matrix, the breast abnormality location based on the second mammographic image.

4. The method of claim 3, further comprising:
reducing a size of the mass section matrix and the normal section matrix using machine learning to obtain reduced matrices,
wherein the reduced matrices are used to detect the breast abnormality.

5. The method of claim 4, wherein reducing the size comprises using k-means clustering.

6. The method of claim 5, wherein the reducing the size comprises reducing a number of rows using k-means clustering and reducing a number of columns by selecting a set of principal components.

7. The method of claim 3, wherein the second region is defined by a mass detection sliding window parameter.

8. The method of claim 1, further comprising:
for each target pixel of at least a subset of target pixels in the second mammographic image:
identifying a region for the target pixel based on mass detection sliding window parameters to create a row,
reducing a size of the row to obtain a reduced row, and
applying machine learning to the reduced row to obtain a pixel score for target pixel;
grouping the pixel score of at least the subset of target pixels to generate an image score matrix for the enhanced image; and
detecting the breast abnormality location using the image score matrix.

9. The method of claim 8, further comprising:
performing the image enhancement on the region to obtain an enhanced region;
within the enhanced region, obtaining a sub-region corresponding to the each target pixel based on mass detection sliding window parameters; and
converting the sub-region to a row in the image score matrix.

10. The method of claim 8, further comprising:
applying an image smoothing over the image score matrix to obtain a smoothed image;
identifying a location of a maxima in smoothed image;
wherein the breast abnormality location is a location of the maxima.

11. The method of claim 1, further comprising:
for each sliding window size of a plurality of sliding window sizes:
for each target pixel of at least a subset of target pixels in the second mammographic image:
identifying a region for the target pixel based on the sliding window size to create a row,
reducing a size of the row to obtain a reduced row, and
applying machine learning to the reduced row to obtain a pixel score for target pixel; and
grouping the pixel score of at least the subset of target pixels to generate an image score matrix for the enhanced image;
combining the image score matrix of the plurality of sliding window sizes into a combined matrix; and
detecting the breast abnormality location using the combined matrix.

12. The method of claim 1, wherein detecting the breast abnormality comprises detecting a set of pixels having a greater than a first threshold gray level and having a plurality of neighbor pixels with less than a second threshold gray level.

13. The method of claim 1, further comprising:
apply an inner filter to a target pixel to obtain a high grey level contrast value;
apply an outer filter to the target pixel to obtain a low grey level contrast value;
subtract the low grey level contrast value from the high grey level contrast value to obtain a resulting contrast value; and
mark the target pixel for microcalcification when the resulting contrast value exceeds threshold, wherein the target pixel is the breast abnormality location.

14. The method of claim 1, wherein the breast abnormality location corresponds to at least one of a mass and a microcalcification.

15. The method of claim 1, wherein detecting the breast abnormality location is performed in response to a dynamically linked library call.

16. The method of claim 1, wherein the first mammographic image is received via the Internet by a server, wherein the server generates the second mammographic image.

17. The method of claim 1, wherein at least one selected from a group consisting of the first mammographic image and the second mammographic image is received via the Internet by a server, wherein the server detects the breast abnormality.

18. The method of claim 1, further comprising:
displaying the second mammographic image with the breast abnormality location marked.

19. A system comprising:
a data repository for storing a first mammographic image; and
a computer processor connected to the data repository, the computer processor for executing cancer detection software, the cancer detection software comprising:
an image enhancer, wherein the image enhancer is configured to:
obtain, from the data repository, a first mammographic image comprising a plurality of original pixels; and
generate a second mammographic image by enhancing the first mammographic image, wherein enhancing the first mammographic image comprises:
for each original pixel in at least a subset of the plurality of original pixels:
generating a histogram for a first region surrounding the original pixel, the first region defined by an enhancement sliding window, and
revising, using the histogram, a value of the original pixel to obtain a revised value, the generating the histogram and revising the value comprising:

calculating, for the first region, a probability density function;

calculating, for the first region, an exponential density function;

calculating, for the first region, a cumulative distribution function using the probability density function;

calculating, for the first region, a cumulative exponential density function using the exponential density function; and calculating the revised value for the first region using the cumulative distribution function and the cumulative exponential density function, and storing the revised value in the second mammographic image, and wherein the cancer detection software is configured to detect a breast abnormality location based on the second mammographic image.

20. A non-transitory computer readable medium comprising computer readable program code for:

receiving a first mammographic image comprising a plurality of original pixels;

generating a second mammographic image by enhancing the first mammographic image, wherein enhancing the first mammographic image comprises:

for each original pixel in at least a subset of the plurality of original pixels:

generating a histogram for a first region surrounding the original pixel, the first region defined by an enhancement sliding window, and revising, using the histogram, a value of the original pixel to obtain a revised value, the generating the histogram and revising the value comprising:

calculating, for the first region, a probability density function;

calculating, for the first region, an exponential density function;

calculating, for the first region, a cumulative distribution function using the probability density function;

calculating, for the first region, a cumulative exponential density function using the exponential density function; and calculating the revised value for the first region using the cumulative distribution function and the cumulative exponential density function, and storing the revised value in the second mammographic image; and detecting a breast abnormality location based on the second mammographic image.

* * * * *

UNITED STATES PATENT AND TRADEMARK OFFICE
CERTIFICATE OF CORRECTION

PATENT NO. : 10,789,712 B2
APPLICATION NO. : 16/031426
DATED : September 29, 2020
INVENTOR(S) : Waleed Ahmed Yousef It is certified that error appears in the above-identified patent and that said Letters Patent is hereby corrected as shown below:

On the Title Page

Item (72) Inventor:, the word -- City -- should be inserted after "Nasr".

In the Specification

Column 12, Line 34, the word "grey" should read -- gray --.

Column 14, Line 31, the word "grey" should read -- gray --.

Column 14, Line 33, the word "grey" should read -- gray --.

Column 14, Line 36, the word "grey" should read -- gray --.

Column 14, Line 38, the word "grey" should read -- gray --.

Column 14, Line 41, the word "grey" should read -- gray --.

Column 14, Line 42, the word "grey" should read -- gray --.

Column 15, Line 29, the word "grey" should read -- gray --.

In the Claims

Claim 2, Column 20, Line 61, the word "scoring" should read -- storing --.

Claim 3, Column 21, Line 6, the word -- to -- should be inserted between the words "corresponding" and "the".

Signed and Sealed this
Eighth Day of December, 2020

Andrei Iancu
*Director of the United States Patent and Trademark Office*

Claim 3, Column 21, Line 11, the word -- to -- should be inserted between the words "corresponding" and "the".

Claim 8, Column 21, Line 39, the word -- the -- should be inserted between the words "for" and "target".

Claim 10, Column 21, Line 56, the word -- the -- should be inserted between the words "in" and "smoothed".

Claim 13, Column 22, Line 16, the word "grey" should read -- gray --.

Claim 13, Column 22, Line 18, the word "grey" should read -- gray --.

Claim 13, Column 22, Line 20, the word "grey" should read -- gray --.

Claim 13, Column 22, Line 21, the word "grey" should read -- gray --.